(12) United States Patent
Hernandez

(10) Patent No.: US 12,249,234 B2
(45) Date of Patent: Mar. 11, 2025

(54) SYSTEMS, DEVISES, AND METHODS INCLUDING A HEARTBEAT MIMETIC

(71) Applicant: THUMP, INC., Atlanta, GA (US)

(72) Inventor: Fernando Juan Hernandez, Atlanta, GA (US)

(73) Assignee: THUMP, INC., Atlanta, GA (US)

( * ) Notice: Subject to any disclaimer, the term of this patent is extended or adjusted under 35 U.S.C. 154(b) by 0 days.

(21) Appl. No.: 17/775,125

(22) PCT Filed: Nov. 7, 2020

(86) PCT No.: PCT/US2020/059566
§ 371 (c)(1),
(2) Date: May 6, 2022

(87) PCT Pub. No.: WO2021/092511
PCT Pub. Date: May 14, 2021

(65) Prior Publication Data
US 2022/0383713 A1    Dec. 1, 2022

Related U.S. Application Data

(60) Provisional application No. 62/932,349, filed on Nov. 7, 2019.

(51) Int. Cl.
*G08B 7/00*    (2006.01)
*G08C 17/02*    (2006.01)
(Continued)

(52) U.S. Cl.
CPC ............... *G08B 7/00* (2013.01); *G08C 17/02* (2013.01); *G10K 15/02* (2013.01); *H04R 1/028* (2013.01); *H04R 3/00* (2013.01); *A61B 5/6801* (2013.01)

(58) Field of Classification Search
CPC .......... G08B 7/00; G08C 17/02; G10K 15/02; H04R 1/028; H04R 3/00; A61B 5/6801
See application file for complete search history.

(56) References Cited

U.S. PATENT DOCUMENTS

2008/0243041 A1    10/2008 Brenner et al.
2014/0039452 A1    2/2014 Bangera et al.
(Continued)

FOREIGN PATENT DOCUMENTS

CN    103446654 A    12/2013
JP    2003249867 A    9/2003
(Continued)

OTHER PUBLICATIONS

International Search Report issued Feb. 5, 2021 in PCT/US2020/059566 (2 pages).
(Continued)

*Primary Examiner* — Ryan W Sherwin
(74) *Attorney, Agent, or Firm* — Makor Law Group, PLLC; Ronald Stern

(57) ABSTRACT

Systems, devices, and methods are described for providing, among other things, a device including a heartbeat mimetic unit configured to generate an acoustic stimulus that mimics a heartbeat. In an embodiment, the device includes a warm-touch unit configured to generate a thermal stimulus. In an embodiment, the device includes a controller unit operably coupled to the heartbeat mimetic unit and the warm touch unit, the controller unit configured to activate at least one of the heartbeat mimetic unit or the warm-touch unit. In an embodiment, the device includes a communication unit configured to exchange at least one of heartbeat mimetic data or warm-touch data with a remote network.

18 Claims, 14 Drawing Sheets

(51) Int. Cl.
*G10K 15/02* (2006.01)
*H04R 1/02* (2006.01)
*H04R 3/00* (2006.01)
*A61B 5/00* (2006.01)

(56) References Cited

U.S. PATENT DOCUMENTS

| | | | |
|---|---|---|---|
| 2014/0340206 A1* | 11/2014 | Bugg, Jr. | G08B 7/00 340/326 |
| 2015/0156581 A1 | 6/2015 | Efrati et al. | |
| 2015/0328082 A1* | 11/2015 | Jiang | A61H 23/02 600/38 |
| 2016/0249200 A1 | 8/2016 | Liu et al. | |
| 2017/0012972 A1* | 1/2017 | Tanaka | G06F 1/1698 |
| 2017/0332442 A1 | 11/2017 | Strecker | |
| 2021/0223817 A1* | 7/2021 | Ishii | G06F 1/163 |

FOREIGN PATENT DOCUMENTS

| | | |
|---|---|---|
| SE | 1400575 A1 | 6/2016 |
| WO | 2003/090889 A1 | 11/2003 |
| WO | 2017/204242 A1 | 11/2017 |

OTHER PUBLICATIONS

Written Opinion issued Feb. 5, 2021 in PCT/US2020/059566 (6 pages).
Arvin et al., "Frequency shifting approach towards textual transcription of heartbeat sounds", Biol Proced Online. Oct. 4, 2011;13:7. doi: 10.1186/1480-9222-13-7.
European Extended European Search Report issued Oct. 9, 2023 in EP 20886096.5 (8 pages).
International Preliminary Report on Patentability issued in PCT/US2020/0529566 on May 10, 2022 (7 pages).

* cited by examiner

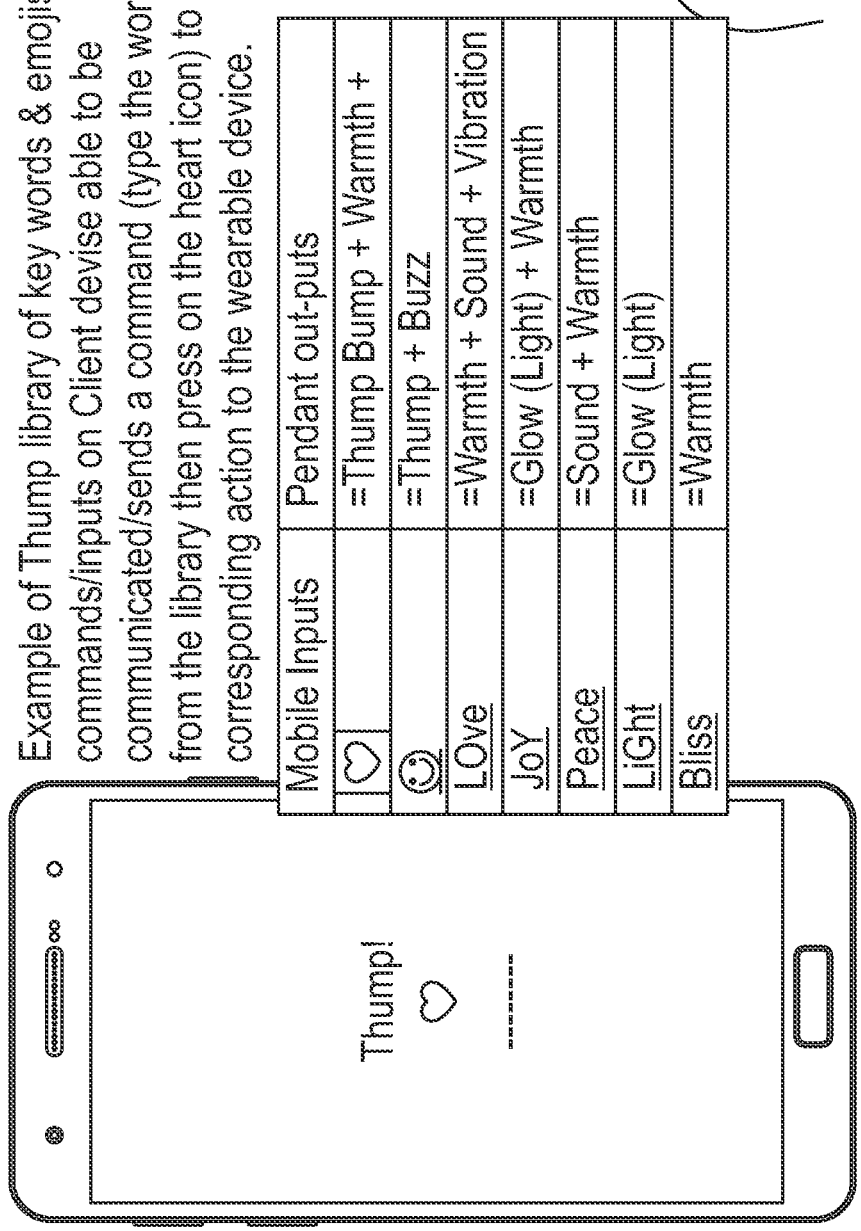

Example of Thump library of key words & emojis commands/inputs on Client devise able to be communicated/sends a command (type the word from the library then press on the heart icon) to corresponding action to the wearable device.

| Mobile Inputs | Pendant out-puts |
|---|---|
| ♡ | =Thump Bump + Warmth + |
| ☺ | =Thump + Buzz |
| LOve | =Warmth + Sound + Vibration |
| JoY | =Glow (Light) + Warmth |
| Peace | =Sound + Warmth |
| LiGht | =Glow (Light) |
| Bliss | =Warmth |

FIG. 3C

Client devise sends a command (press on the heart icon) to wearable device. Wearable receives command to mimetics a Thump Love beat. It is configured to generate an acoustic stimulus that mimics a heartbeat with sound or vibration.

SYSTEMS, DEVISES, AND METHODS INCLUDING A HEARTBEAT MIMETIC

CROSS-REFERENCE TO RELATED APPLICATION(S)

The present invention is filed under 35 U.S.C. § 371 as the U.S. national phase of International Application No. PCT/US2020/059566, filed on Nov. 7, 2020, which designated the United States and claims the benefit of priority of U.S. Provisional Application No. 62/932,349, filed on Nov. 7, 2019, the entire contents of each of which is hereby incorporated by reference in their entirety for any purpose.

SUMMARY

In an aspect, the present disclosure is directed to, among other things, a wearable device including a heartbeat mimetic unit configured to generate an acoustic stimulus that mimics a heartbeat. In an embodiment, the wearable device includes a warm-touch unit configured to generate a thermal stimulus. In an embodiment, the wearable device includes a controller unit operably coupled to the heartbeat mimetic unit and the warm touch unit, the controller unit configured to activate at least one of the heartbeat mimetic unit or the warm-touch unit. In an embodiment, the wearable device includes a communication unit configured to exchange at least one of heartbeat mimetic data or warm-touch data with a remote network. In an embodiment, the wearable device includes a communication unit configured to actuate a discovery protocol that allows the wearable device and a remote enterprise to identify each other and to negotiate one or more pre-shared keys. In an embodiment, the wearable device includes a communication unit including circuitry for actuating a discovery protocol that allows the wearable device and a remote application server to identify each other and negotiate information.

In an aspect, the present disclosure is directed to, among other things, a device, including a controller operably coupled to a heartbeat mimetic device and a warm-touch device, the controller configured to activate delivery of at least one of an acoustic stimulus that mimics a heartbeat, or a thermal stimulus responsive to receiving one or more control commands from a remote device.

In an aspect, the present disclosure is directed to, among other things, a system including computational circuitry configured to exchange at least one of heartbeat mimetic data or warm-touch data with a remote device. In an embodiment, the system includes computational circuitry configured to generate a virtual display representing at least one heartbeat mimetic data sender or warm-touch data sender responsive to exchanging the at least one of heartbeat mimetic data or warm-touch data with a remote device.

In an aspect, the present disclosure is directed to, among other things, a system including computational circuitry configured to remotely activate a wearable device to generate one or more acoustic stimuli that mimics a heartbeat. In an embodiment, the system includes computational circuitry configured to remotely activate the wearable device to generate one or more thermal stimulus. In an embodiment, the system includes computational circuitry configured to remotely activate the wearable device to generate a virtual display including one or more instances identifying a sender associated with remotely activating a wearable device to generate acoustic stimuli or remotely activating the wearable device to generate thermal stimuli.

In an aspect, the present disclosure is directed to, among other things, a method comprising exchanging at least one of heartbeat mimetic data or warm-touch data with a remote device. In an embodiment, the method includes generating a virtual display representing at least one heartbeat mimetic data sender or warm-touch data sender responsive to exchanging the at least one of heartbeat mimetic data or warm-touch data with a remote device.

In an aspect, the present disclosure is directed to, among other things, a method comprising generating an acoustic stimulus that mimics a heartbeat responsive to receiving one or more wireless commands. In an embodiment, the method includes generating a thermal stimulus receiving one or more wireless commands.

BRIEF DESCRIPTION OF THE FIGURES

FIGS. 3A-3L are schematic diagram of a system according one or more embodiments.

Figure 1:
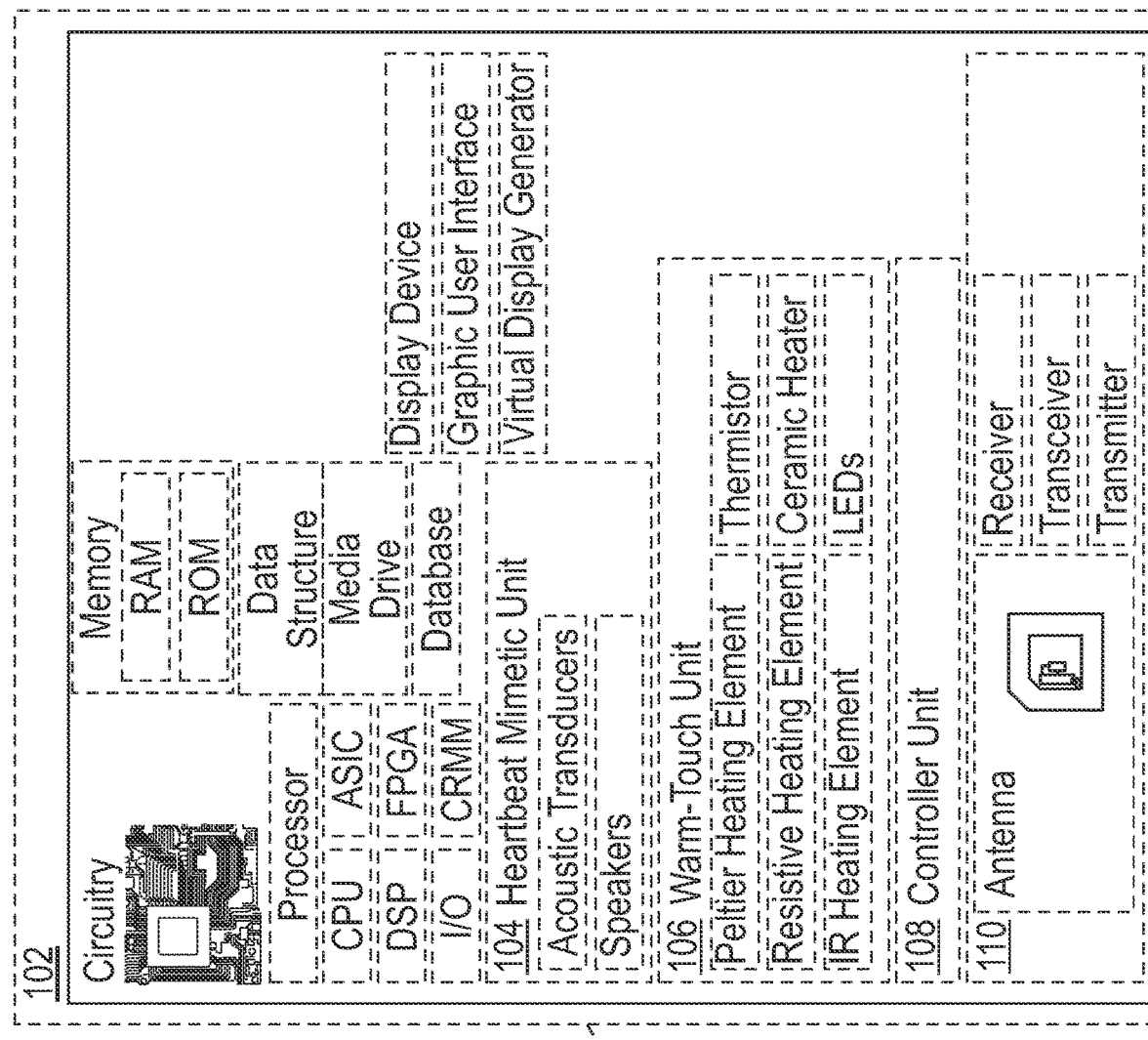
FIG. 1 is a schematic diagram of a wearable device according one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here.

DETAILED DESCRIPTION

Social media platforms allow people to communicate create, interact, share, and exchange information in virtual communities and networks. They connect people to friends, relatives, and acquaintances by a simple tapping of a finger. Social media platforms enable users to express emotions and feelings towards each other in a variety of ways including text, tweets, emojis, stickers, and animated pictures (GIF). But at times these convenient platforms lessen the quality of the human connection.

Figure 2:
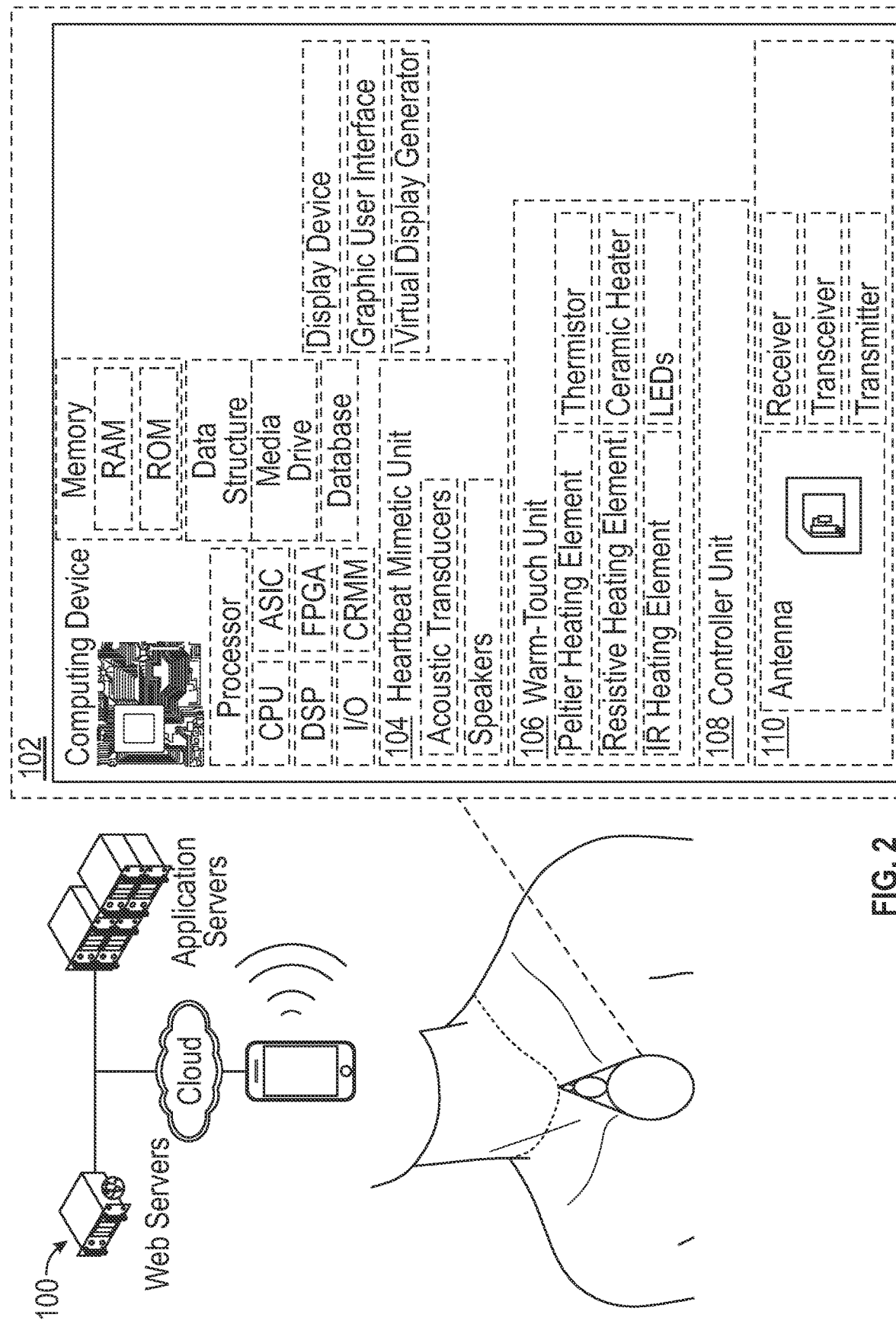
FIG. 2 is a schematic diagram of a wearable device according one embodiment.
Figure 3A:
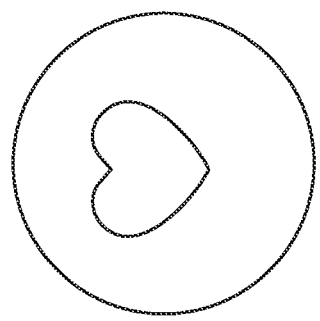
Figure 3B:
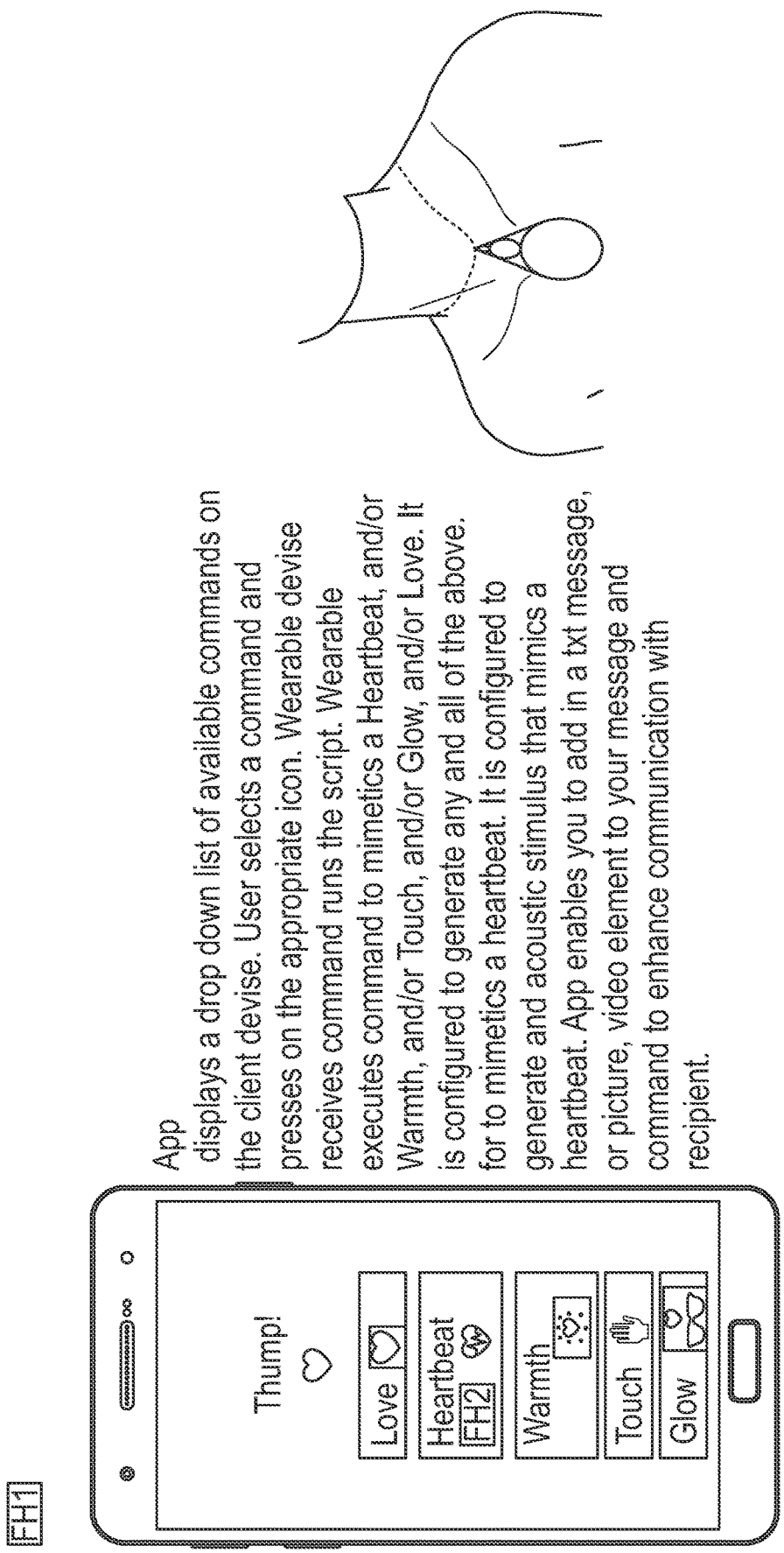
Figure 3D:
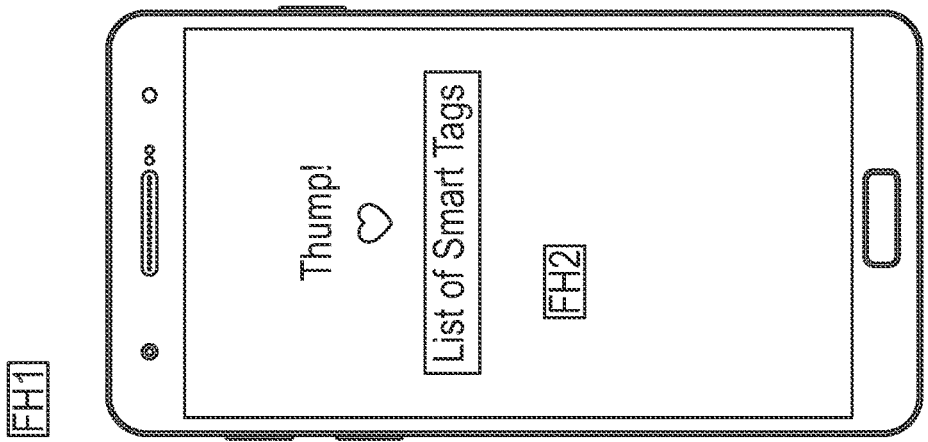
Figure 3E:
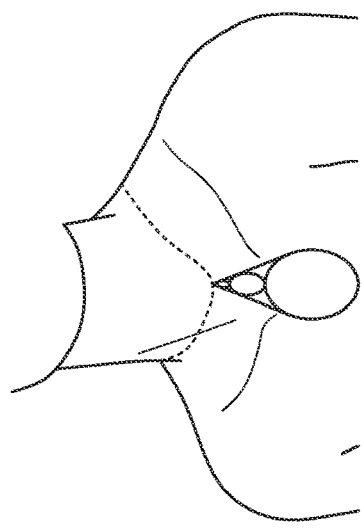
Figure 3E:
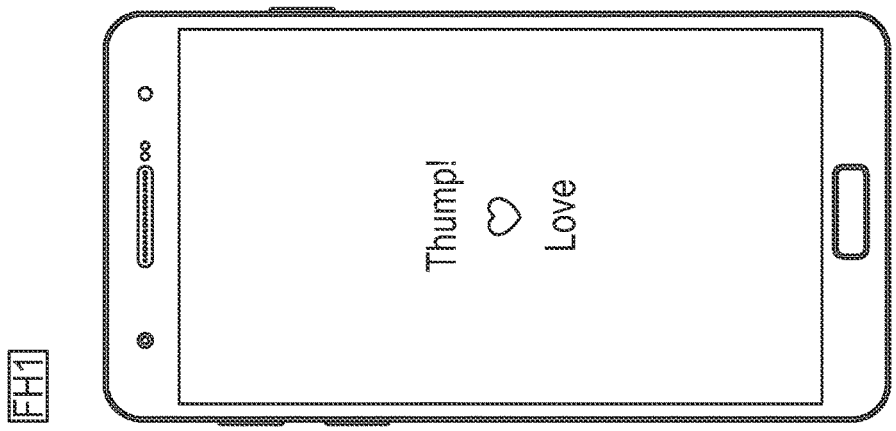
Figure 3F:
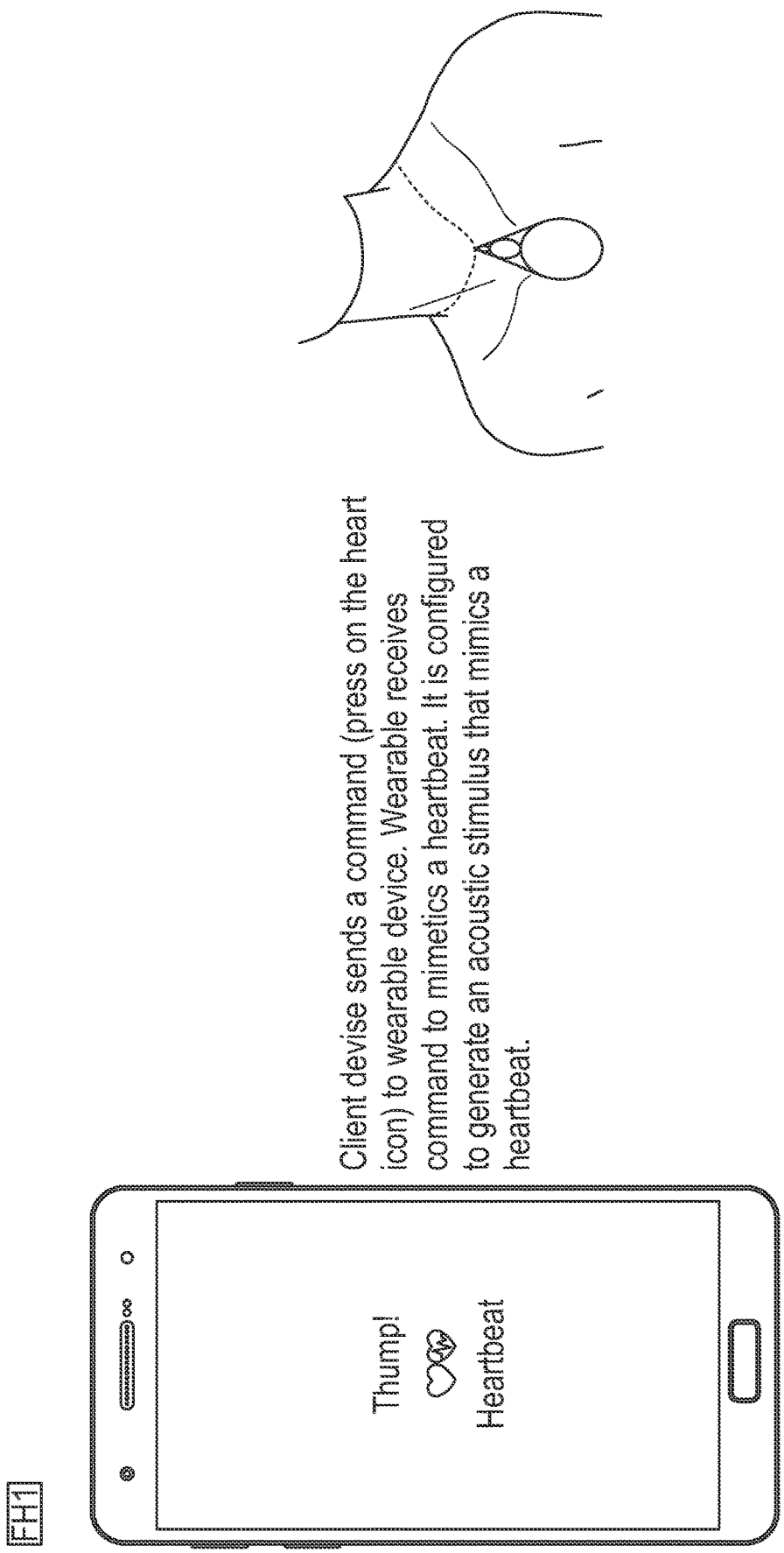
Figure 3G:
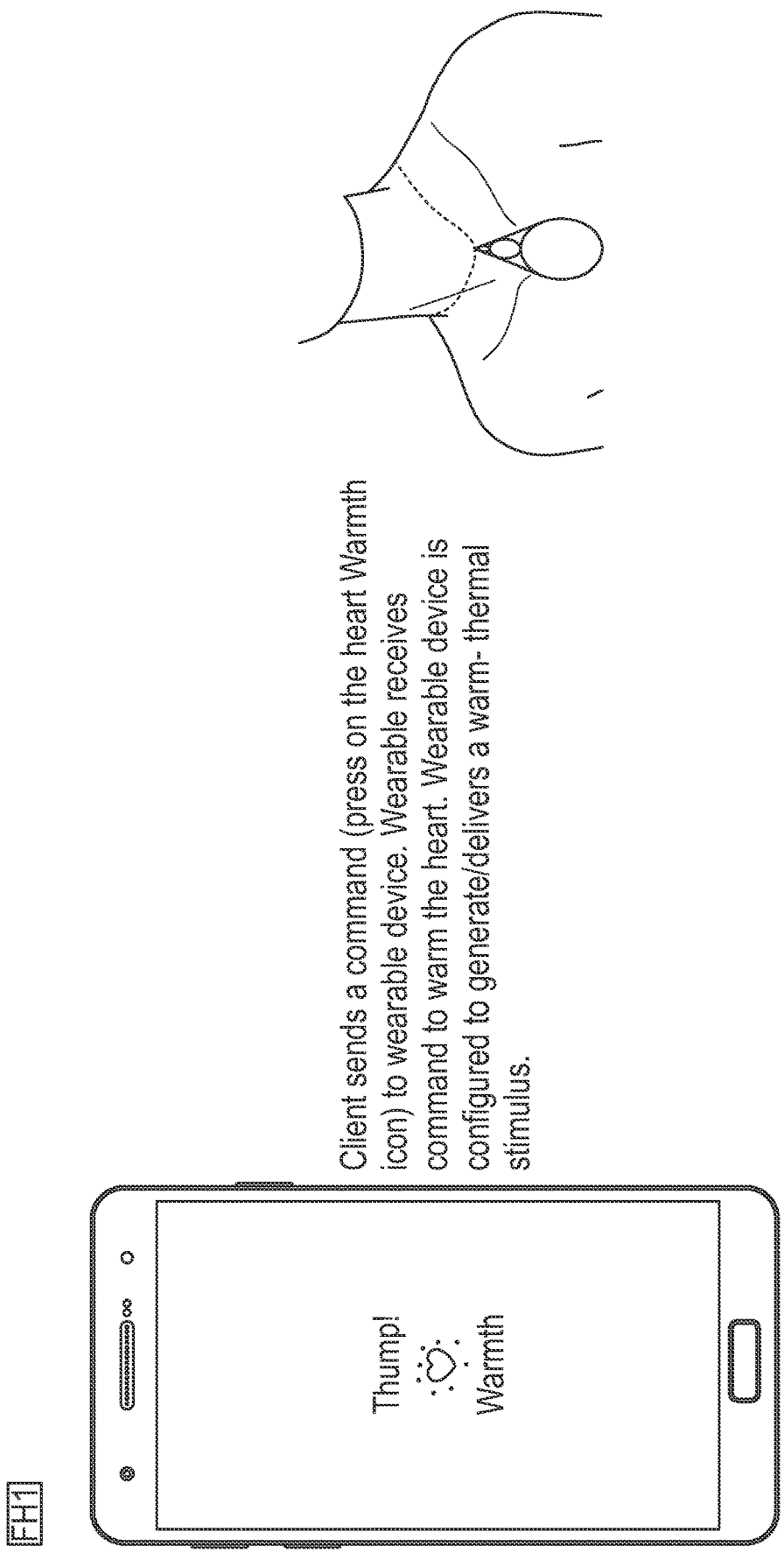
Figure 3H:
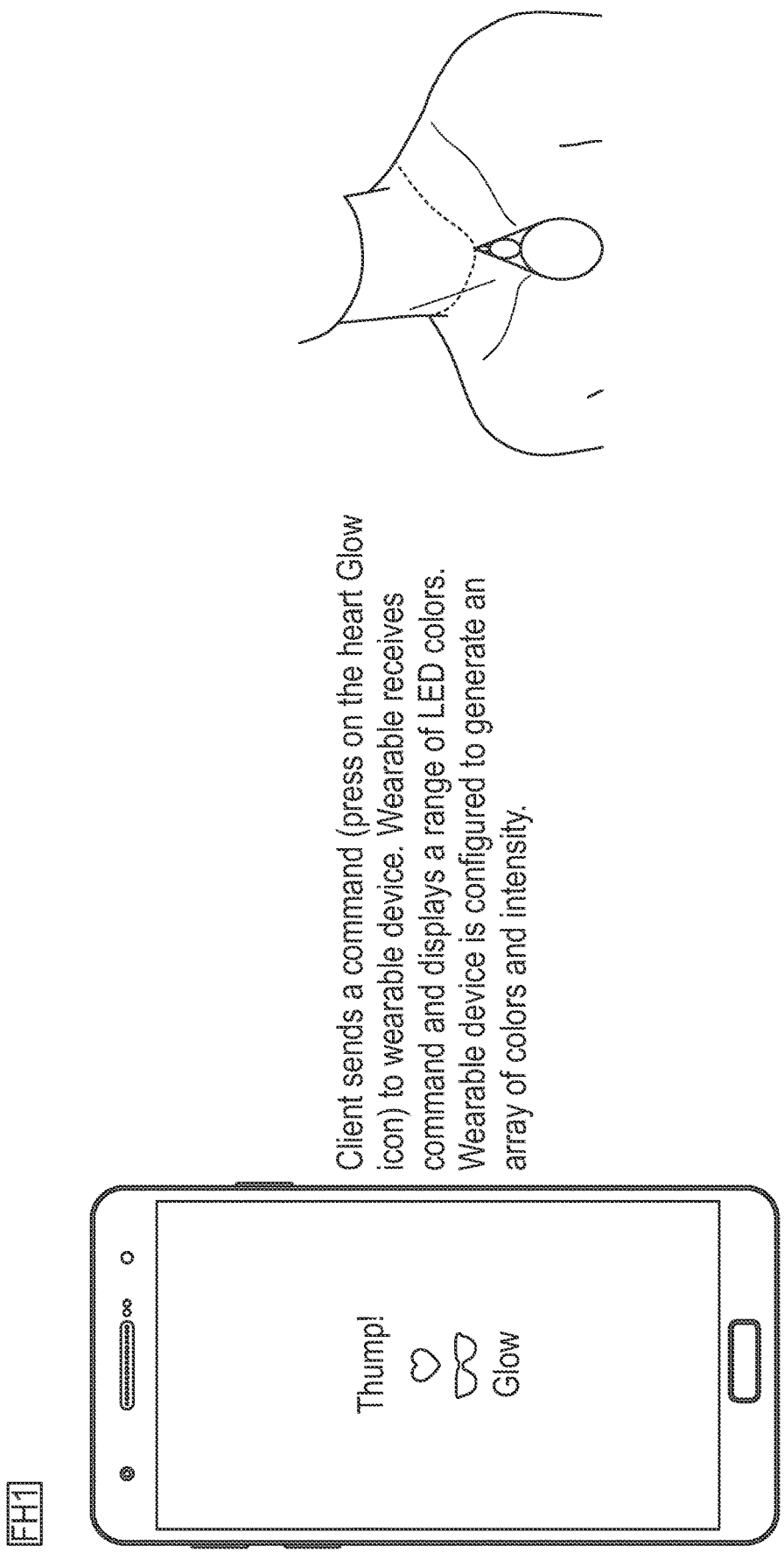
Figure 3I:
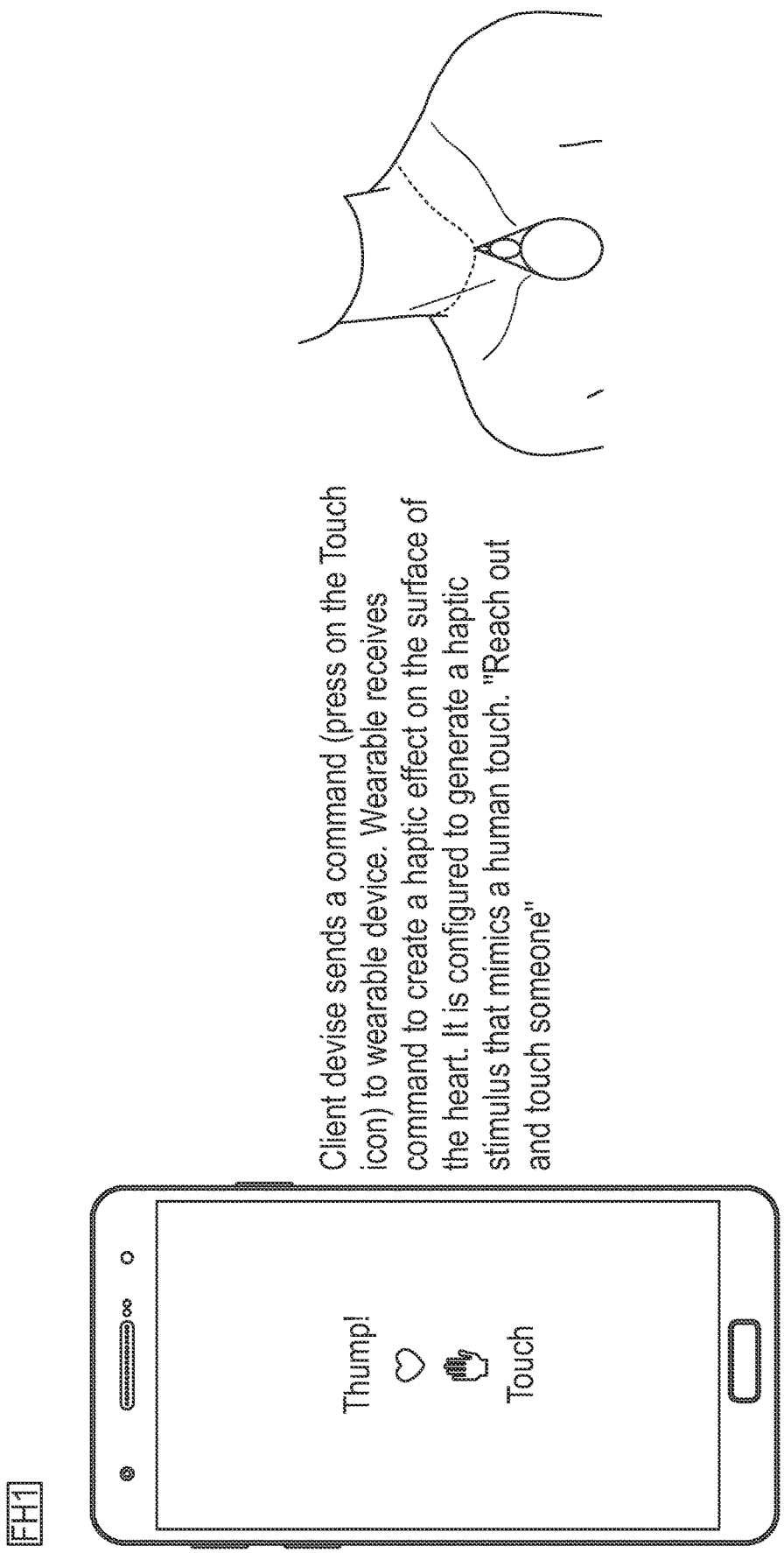
Figure 3J:
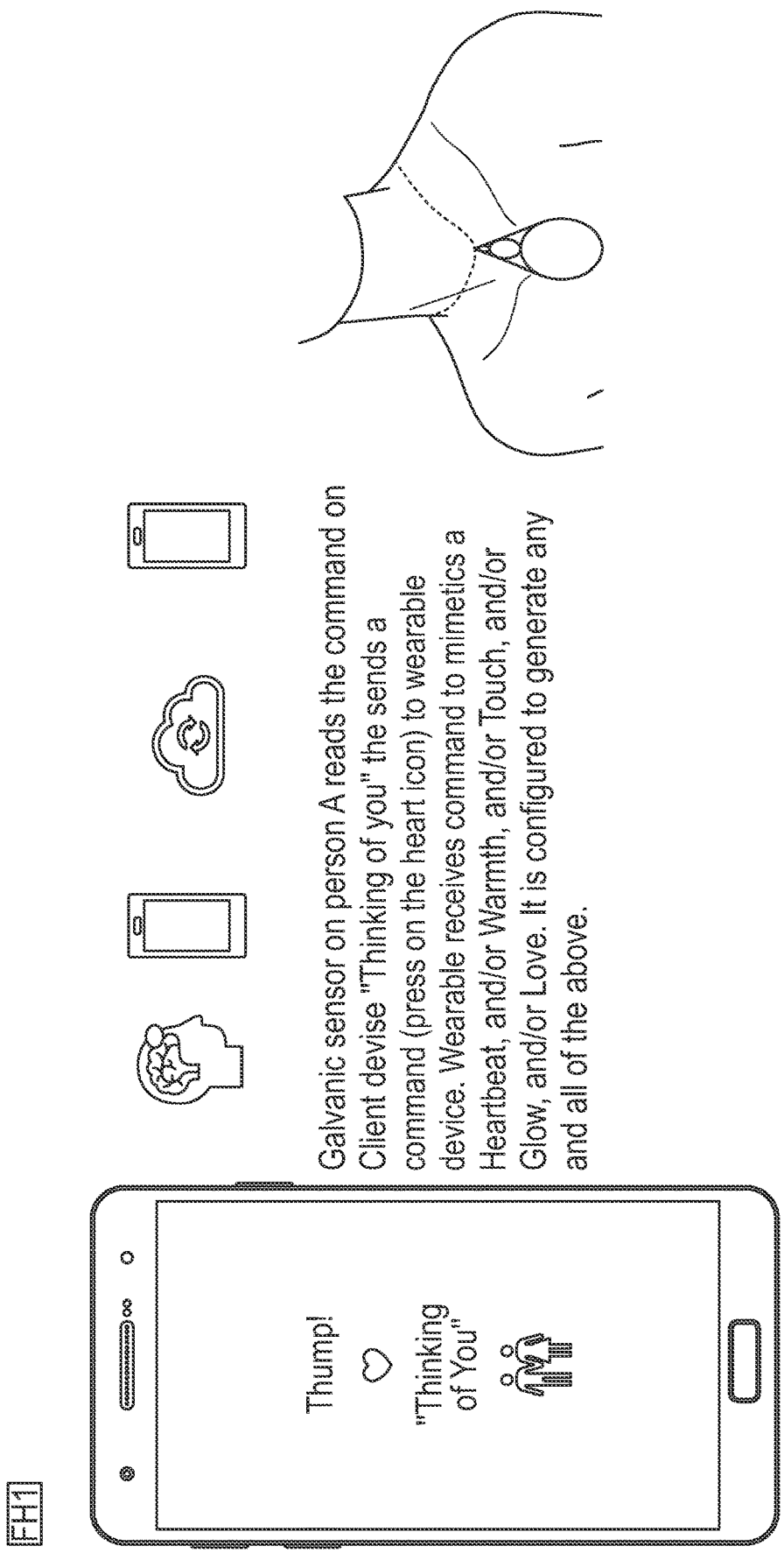
Figure 3K:
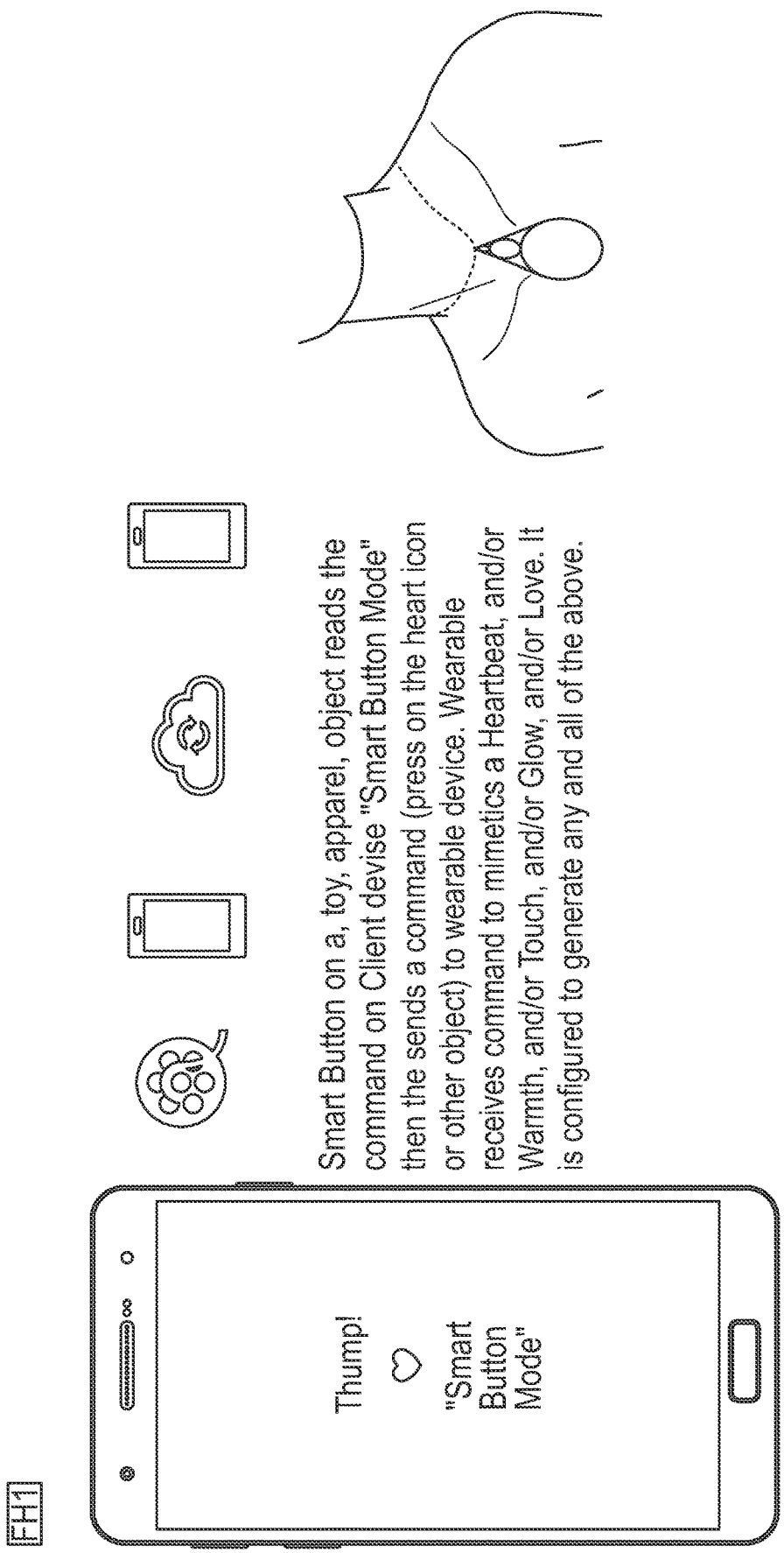
Figure 3L:
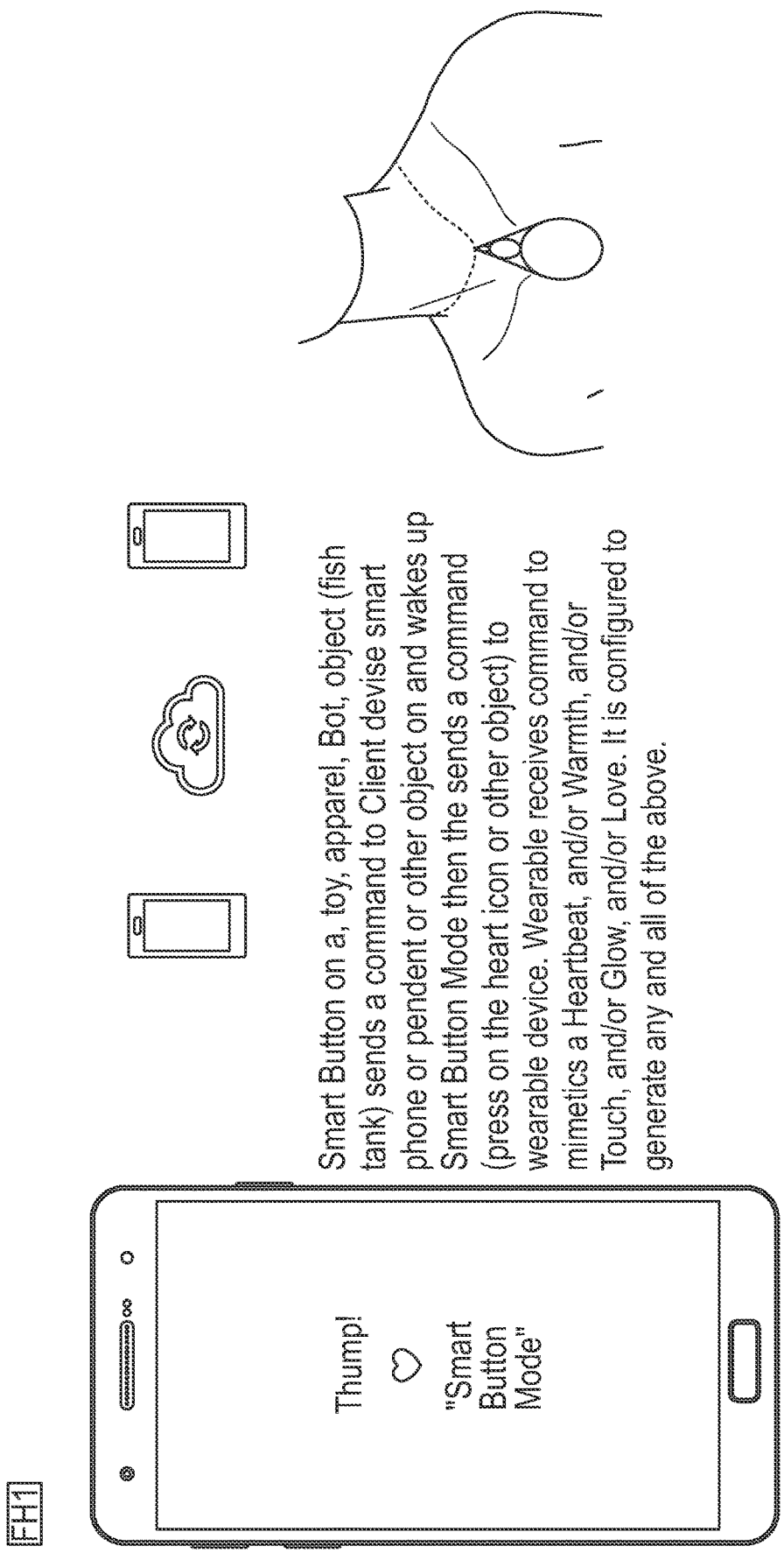

FIGS. 1 and 2 show a system 100 for implementing one or more technologies and methodologies for enhancing a virtual communication experience by providing more humanistic ways to convey sentiments or emotions using hardware, firmware, and software components; transforming feelings and emotions in a way that delivers a greater sense of connectedness by novel use of technology, and the like. In an embodiment, the system 100 includes a wearable device 102.

In an embodiment, the wearable device 102 includes a heartbeat mimetic unit 104 configured to generate an acoustic stimulus that mimics a heartbeat. In an embodiment, the heartbeat mimetic unit 104 includes electrical circuitry and at least one transducer configured to generate acoustic stimulus that mimics a heartbeat. In an embodiment, the heartbeat mimetic unit 104 includes computational circuitry configured to generate a pulsed acoustic stimulus that mimics a human heartbeat.

In an embodiment, the heartbeat mimetic unit 104 includes electrical circuitry configured to generate a pulsed acoustic stimulus having at least a first heart sound and second heart sound, the first sound comprising a first music octave and the second sound comprising a second music octave different from the first music octave. In an embodiment, the heartbeat mimetic unit 104 includes computational circuitry configured to generate an acoustic stimulus having a peak emission frequency ranging from about 20 Hertz to about 150 Hertz. In an embodiment, the heartbeat mimetic unit 104 includes computational circuitry configured to generate one or more heart sound pulses, each heart sound pulse having a duration ranging from about 50 milliseconds to about 150 milliseconds. In an embodiment, the heartbeat mimetic unit 104 includes computational circuitry configured to generate one or more heart sound pulses, each heart sound pulse having a duration of about 100 milliseconds. (see e.g., https://www.ncbi.nlm.nih.gov/pmc/articles/PMC3396354/; which is incorporated herein by reference in full)

In an embodiment, the wearable device 102 includes a warm-touch unit 106 configured to generate a thermal stimulus. In an embodiment, the warm-touch unit 106 includes electrical circuitry configured to generate a thermal stimulus. In an embodiment, the warm-touch unit 106 includes electrical circuitry configured to generate a thermal stimulus ranging from about 32° C. to about 36° C. In an embodiment, the warm-touch unit 106 includes one or more resistive heating elements. In an embodiment, the warm-touch unit 106 includes one or more Peltier heating elements. In an embodiment, the warm-touch unit 106 includes one or more infrared heating elements. In an embodiment, the warm-touch unit 106 includes one or more thermal light emitting diodes.

In an embodiment, the wearable device 102 includes a controller unit 108 operably coupled to the heartbeat mimetic unit and the warm touch unit, the controller unit configured to activate at least one of the heartbeat mimetic unit or the warm-touch unit. In an embodiment, the wearable device 102 includes a communication unit 110 configured to exchange at least one of heartbeat mimetic data or warm-touch data with a remote network. In an embodiment, the wearable device 102 includes a communication unit 110 configured to exchange at least one of heartbeat mimetic data or warm-touch data with one or more client devices.

In an embodiment, the communication unit 110 includes at least one of transceiver circuitry, transmitter circuitry, or receiver circuitry configured to exchange at least one of heartbeat mimetic data or warm-touch data with a remote network. In an embodiment, the wearable device 102 includes a communication unit 110 configured to actuate a discovery protocol that allows the wearable device and a remote enterprise to identify each other and to negotiate one or more pre-shared keys. In an embodiment, the wearable device 102 includes a communication unit 110 including circuitry for actuating a discovery protocol that allows the wearable device and a remote application server to identify each other and negotiate information.

In an embodiment, a device includes a controller operably coupled to a heartbeat mimetic device and a warm-touch device, the controller configured to activate delivery of at least one of an acoustic stimulus that mimics a heartbeat, or a thermal stimulus responsive to receiving one or more control commands from a remote device. In an embodiment, the device includes a hardware unit that lights up with personalized color when receiving a love message. In an embodiment, users experience an emotional connection with one another that resembles a physical interaction. In an embodiment, the device comprises a smart Jewelry device. In an embodiment, the device takes the form of a Charm bracelet, Coin (touch), Cross, Star of David, Other, Earbuds (touch), Earrings, Hair Clip, Heart shaped pendent (other pendants), Heart Urn, Key chain, Money clip, Objects used in piercing, Pen (touch), Pet Collar, Picture frame (touch), Ring, Sacred Heart, Smart Lock and Key (Heart female/key male), Tie clip, Watch, Wearable sensor, Wearable tattoo, or the like. In an embodiment, the device comprises Smart buttons that receive and send information/data. In an embodiment, the device comprises Clip on to clothing, shoes, toys, toy animals, etc. In an embodiment, the device comprises AI Smart Tags (Fish Tank, Self-action idea). In an embodiment, the device comprises Decorative domed emblems. In an embodiment, the device comprises a Fob, Decorative badges, Trim, Information Labels, Overlays. In an embodiment, the device comprises Smart glasses, Smart skin (overlay, coating), Smart containers, Neurables, or the like.

In an embodiment, the device includes one or more functionalities. Non-limiting examples of functionalities include NUI (Natural User Interface), Neurable interface (see Neurable), Gesture interface (see Hug Innovation), Speech interface (smart speaker key words), Touch interface, Haptic interface (see super haptics mini sound canon), Bi-directional interface example: (Pendent sends information to smart button(s)/bott(s) that receive the information and takes an action. Or the other way, smart button(s)/bott(s) sends information to the pendent), Uni-directional interface, and the like.

In an embodiment, the device includes one or more interface of the elements. Non-limiting examples of Interface of the elements, include Neurable, Gesture commands/library, SMS Txt, IM, Voice to TxT, and the like. In an embodiment, the device includes one or more Processors, Circuitry, Power Source, Receiver, Transmitter, Wireless interface (Bluetooth, WIFI, RFID), NUI (gesture, touch, speech, mental thought), Neuro Detector, Smart speaker interface (speaker could be stand alone in some embodiments), Heating/Cooling (Peltier devise), Screen, Recorder, Light (Minnie LED), Haptic touch, Camera, Accelerometer, Scent sachet, Crystal, Liquid, and the like.

In an embodiment, a system includes computational circuitry configured to exchange at least one of heartbeat mimetic data or warm-touch data with a remote device. In an embodiment, the system includes computational circuitry configured to generate a virtual display representing at least one heartbeat mimetic data sender or warm-touch data sender responsive to exchanging the at least one of heartbeat mimetic data or warm-touch data with a remote device.

In an embodiment, a system includes computational circuitry configured to remotely activate a wearable device to generate one or more acoustic stimuli that mimics a heartbeat. In an embodiment, the system includes computational circuitry configured to remotely activate the wearable device to generate one or more thermal stimulus. In an embodiment, the system includes computational circuitry configured to remotely activate the wearable device to generate a virtual display including one or more instances identifying a sender associated with remotely activating a wearable device to generate acoustic stimuli or remotely activating the wearable device to generate thermal stimuli.

In an embodiment, a method includes exchanging at least one of heartbeat mimetic data or warm-touch data with a remote device. In an embodiment, the method includes generating a virtual display representing at least one heartbeat mimetic data sender or warm-touch data sender responsive to exchanging the at least one of heartbeat mimetic data or warm-touch data with a remote device. In an embodiment, a method includes generating an acoustic stimulus that mimics a heartbeat responsive to receiving one or more wireless commands; and generating a thermal stimulus receiving one or more wireless commands.

In an embodiment, circuitry includes, among other things, one or more computing devices 108 such as a processor (e.g., a microprocessor, and the like), a central processing unit (CPU), a digital signal processor (DSP), an application-specific integrated circuit (ASIC), field programmable gate array (FPGA), or the like, or any combinations thereof, and can include discrete digital or analog circuit elements or electronics, or combinations thereof. In an embodiment, circuitry includes one or more ASICs having a plurality of predefined logic components. In an embodiment, circuitry includes one or more FPGAs having a plurality of programmable logic components.

In an embodiment, circuitry includes one or more electrical components operably coupled (e.g., communicatively, electromagnetically, magnetically, ultrasonically, optically, inductively, electrically, capacitively coupled, and the like) to each other. In an embodiment, circuitry includes one or more remotely located components. In an embodiment, remotely located components are operably coupled via wireless communication. In an embodiment, remotely located components are operably coupled via one or more receivers, transceivers 117, or transmitters, antennas, or the like.

In an embodiment, circuitry includes one or more network elements. Non-limiting examples of network elements include Local Area Networks (LANs), network gateway systems, network usage servers, Wide Area Networks (WANs), wireless base stations, wireless relays, and the like. In an embodiment, circuitry includes computer and communication platforms that include data Input/Output (I/O) transceivers, digital processing circuitry, data storage memories, various software components, and the like.

In an embodiment, circuitry includes one or more memory devices that, for example, store instructions or data. Non-limiting examples of one or more memory devices include volatile memory (e.g., Random Access Memory (RAM), Dynamic Random-Access Memory (DRAM), or the like); non-volatile memory (e.g., Read-Only Memory (ROM), Electrically Erasable Programmable Read-Only Memory (EEPROM), Flash memory, or the like); persistent memory; or the like. The one or more memory devices can be coupled to, for example, one or more computing devices by one or more instructions, data, or power buses.

In an embodiment, where applicable, circuitry includes peripheral devices such as Bluetooth, Wi-Fi, USB (or other wireless or wired network communication peripherals cable of data exchange with remote client and server computers), and cellular connectivity to exchange data, exchange control commands, configure the system 100, or remotely monitor system 100 parameters. In an embodiment, circuitry includes one or more user input/output components that are operably coupled to the system 100 to generate a user interface that enables access to all user configurable parameters.

In an embodiment, the system 100 includes circuitry configured to exchange acquire heartbeat mimetic data or warm-touch data with a remote client device and remote server. In an embodiment, the system includes circuitry configured to acquire heartbeat mimetic data or warm-touch data from a plurality of remote client devices. Non-limiting examples of client devices include application interface with smart devices, cell phone devices, computer devices, desktop computer devices, internet of things (IoT) devices, laptop computer devices, managed node devices, mobile client devices, notebook computer devices, remote controllers, smart devices, smart eyewear devices, smart wearable devices, tablet devices, wearable devices, and the like. In an embodiment, a client device includes a computer hardware, firmware, software, and the like that accesses a service made available by a server.

In an embodiment, the device 102 (e.g., smart jewelry, pendant, a wearable device, or the like) is operable to deliver at one or more of a haptic, thermal (e.g., warmth, coolness, temperature change, or the like), or acoustic response based on a trigger. In an embodiment, the device 102 includes computational circuitry configured to deliver one or more of a haptic, thermal, acoustic, electromagnetic radiation stimulus, or the like, based on a target condition.

In an embodiment, the trigger takes the form of computational circuitry including a processor or microprocessor configured to actuate the controller unit 108 based at least on one of a predetermined day/time, non-verbal communication (e.g., responsive to human action and detection by a proximity sensor such as IR sensor or the like), and location-based determination.

In an embodiment, the predetermined day/time includes a scheduled event that is programmable to trigger the controller unit 108 to actuate a particular response from the device 102. In one embodiment, the scheduled event corresponds to, for example, a birthday, holiday, anniversary, etc. In an embodiment, the controller unit 108 actuates the response (e.g., thermal emission via warm-touch unit 106, acoustic response of happy birthday melody via acoustic transducers, play a pre-recorded personalized message, etc.) responsive to one or more inputs associated with a scheduled event. In an embodiment, the controller unit 108 actuates the response responsive to one or more user inputs associated with a pre-programmed event.

In an embodiment, inputs from a proximity sensor, a GPS module, and the like are used to trigger the controller unit 108 to activate delivery of a particular response from the device 102 circuitry. In an embodiment, the proximity sensor and/or GPS module are communicatively coupled to or embedded within the device 102. In an embodiment, the specific response of the device 102 varies based on a particular location of the device 102, as detected by the GPS module. For example, in an embodiment, during operation, when an individual wearing the device 102 enters a church, the GPS module embedded within the device 102 detects an entrance into the Church and trigger a particular location-based greeting response via at least one of the haptic, thermal, and acoustic responses. In an embodiment, the GPS module determines location based on GPS coordinates and by mapping those coordinates to known locations on a predetermined map. In an embodiment, responsive to entering a Church, the device 102 initiates an acoustic response (e.g. church bells). In an embodiment, the user brings his/her hand in close proximity to the device 102 such that the proximity detector actuates the controller unit 108 to activate thermal emission via the warm-touch unit 106 and heat up. In an embodiment, upon the GPS module detecting entrance into a sports stadium, the device 102 initiates an acoustic response in the form of a sports team rally song.

In an embodiment, verbal communication is be used to trigger the controller unit 108 to actuate a response. An illustrative example includes human speech that is detected by the device 102 and parsed by an embedded speech processing module. During a meditation or prayer, responsive to detected 'trigger' words, the controller unit 108 actuates a response that is associated with the 'trigger' word.

For example:
responsive to "feel the divine warmth", warmth is automatically emitted by the warm-touch unit 106;

responsive to "feel the divine touch", haptic feedback is initiated; and responsive to "see the sacred lights", an array of lights are illuminated.

In an embodiment, the device 102 takes the form of at least one of a religious icon, statue, massage/meditation stones, food container, sex toy, baby formula container, wipes, e-makeup, body wash, shampoo, charm bracelet, coin, Cross, Star of David, earbuds, earrings, hair clip, heart shaped pendent (or any other shaped pendants), heart urn, key chain, money clip, objects used in piercing, pen, pet collar, picture frame, ring, sacred heart, smart lock and key (heart female/key male), tie clip, watch, wearable sensor, wearable tattoo, or the like.

In an embodiment, the device 102 comprises smart buttons that receive and send information/data. In an embodiment, the device 102 comprises a clip onto clothing, shoes, toys, toy animals, etc. In an embodiment, the device 102 comprises a robotic pet, an autonomous robot, a robotic pet employing Artificial Intelligence, an interactive robot companion, an artificial Intelligent, companion, and the like. In an embodiment, the device 102 comprises AI smart tags. In an embodiment, the device 102 comprises decorative domed emblems. In an embodiment, the device 102 comprises a Fob, decorative badges, trim, information labels, overlays. In an embodiment, the device 102 comprises smart glasses, smart skin (overlay, coating), smart containers, neurables, or the like.

It will be appreciated the device 102 may function as a node in a network. In an embodiment, a node is capable of creating, receiving, or transmitting information over a communications channel. Examples of nodes include sensors, switches, hubs, and actuators.

It will be further appreciated by those of ordinary skill in the art, that various manifestations are contemplated by the embodiments described herein. The above examples are merely cited to demonstrate some applications of the described embodiments recognizing that additional applications are well within the scope of the embodiments.

The herein described subject matter sometimes illustrates different components contained within, or connected with, different other components. It is to be understood that such depicted architectures are merely examples, and that in fact, many other architectures can be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably coupleable," to each other to achieve the desired functionality. Specific examples of operably coupleable include, but are not limited to, physically mateable, physically interacting components, wirelessly interactable, wirelessly interacting components, logically interacting, logically interactable components, etc.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components, or inactive-state components, or standby-state components, unless context requires otherwise.

The foregoing detailed description has set forth various embodiments of the devices or processes via the use of block diagrams, flowcharts, or examples. Insofar as such block diagrams, flowcharts, or examples contain one or more functions or operations, it will be understood by the reader that each function or operation within such block diagrams, flowcharts, or examples can be implemented, individually or collectively, by a wide range of hardware, software, firmware in one or more machines or articles of manufacture, or virtually any combination thereof. Further, the use of "Start," "End," or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application.

In an embodiment, several portions of the subject matter described herein is implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software and or firmware would be well within the skill of one of skill in the art in light of this disclosure.

In addition, the mechanisms of the subject matter described herein are capable of being distributed as a program product in a variety of forms, and that an illustrative embodiment of the subject matter described herein applies regardless of the signal-bearing medium used to actually carry out the distribution. Non-limiting examples of a signal-bearing medium include the following: a recordable type medium such as magnetic data storage media, non-volatile memory drive "Solid state drive," any potable data storage media, a hard disk drive, a Compact Disc (CD), a Digital Video Disk (DVD), a digital tape, a computer memory, etc.; and a transmission type medium such as a program distribution via remote download over any wired or wireless network.

While aspects of the present subject matter described herein have been shown and described, it will be apparent to the reader that, based upon the teachings herein, changes and modifications can be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances, where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically, a disjunctive word or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), the various operations may be performed in orders other than those that are illustrated or may be performed concurrently. Examples of such alternate orderings includes overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A wearable device, comprising
a heartbeat mimetic unit configured to generate an acoustic stimulus that mimics a heartbeat, the heartbeat mimetic unit including electrical circuitry configured to generate a pulsed acoustic stimulus having at least a first heart sound and a second heart sound, the first heart sound comprising a first music octave and the second heart sound comprising a second music octave different from the first music octave;
a warm-touch unit configured to generate a thermal stimulus; and
a controller unit operably coupled to the heartbeat mimetic unit and the warm touch unit, the controller unit configured to activate at least one of the heartbeat mimetic unit or the warm-touch unit.

2. The wearable device of claim 1, further comprising:
a communication unit configured to exchange at least one of heartbeat mimetic data or warm-touch data with a remote network.

3. The wearable device of claim 2, wherein the communication unit includes at least one of transceiver circuitry, transmitter circuitry, or receiver circuitry configured to exchange at least one of heartbeat mimetic data or warm-touch data with a remote network.

4. The wearable device of claim 1, further comprising:
a communication unit configured to actuate a discovery protocol that allows the wearable device and a remote enterprise to identify each other and to negotiate one or more pre-shared keys.

5. The wearable device of claim 1, further comprising:
a communication unit including circuitry for actuating a discovery protocol that allows the wearable device and a remote application server to identify each other and negotiate information.

6. The wearable device of claim 1, wherein the heartbeat mimetic unit includes electrical circuitry and at least one transducer configured to generate acoustic stimulus that mimics a heartbeat.

7. The wearable device of claim 1, wherein the heartbeat mimetic unit includes computational circuitry configured to generate a pulsed acoustic stimulus that mimics a human heartbeat.

8. The wearable device of claim 1, wherein the heartbeat mimetic unit includes computational circuitry configured to generate an acoustic stimulus having a peak emission frequency ranging from about 20 Hertz to about 150 Hertz.

9. The wearable device of claim 1, wherein the heartbeat mimetic unit includes computational circuitry configured to generate one or more heart sound pulses, each heart sound pulse having a duration ranging from about 50 milliseconds to about 150 milliseconds.

10. The wearable device of claim 1, wherein the heartbeat mimetic unit includes computational circuitry configured to generate one or more heart sound pulses, each heart sound pulse having a duration of about 100 milliseconds.

11. The wearable device of claim 1, wherein the warm-touch unit includes electrical circuitry configured to generate a thermal stimulus.

12. The wearable device of claim 1, wherein the warm-touch unit includes electrical circuitry configured to generate a thermal stimulus ranging from about 32° C. to about 36° C.

13. The wearable device of claim 1, wherein the warm-touch unit includes one or more of resistive heating elements, Peltier heating elements, or infrared heating elements.

14. The wearable device of claim 1, wherein the warm-touch unit includes one or more thermal light emitting diodes.

15. A system, comprising:
computational circuitry configured to remotely activate a wearable device to generate one or more acoustic stimuli that mimics a heartbeat, each acoustic stimuli having a first heart sound and a second heart sound, the first heart sound comprising a first music octave and the second heart sound comprising a second music octave different from the first music octave, and each acoustic stimuli having a duration ranging from about 50 milliseconds to about 150 milliseconds.

16. The system of claim 15, further comprising:

computational circuitry configured to remotely activate the wearable device to generate one or more thermal stimulus.

17. The system of claim 15, further comprising:

computational circuitry configured to remotely activate the wearable device to generate a virtual display including one or more instances identifying a sender associated with remotely activating a wearable device to generate acoustic stimuli or remotely activating the wearable device to generate thermal stimuli.

18. A method comprising:

exchanging at least one of heartbeat mimetic data or warm-touch data with a remote device;

generating a virtual display representing at least one heartbeat mimetic data sender or warm-touch data sender responsive to exchanging the at least one of heartbeat mimetic data or warm-touch data with a remote device;

generating an acoustic stimulus that mimics a heartbeat having at least a first heart sound and a second heart sound, the first heart sound comprising a first music octave and the second heart sound comprising a second music octave different from the first music octave, responsive to receiving one or more wireless commands; and generating a thermal stimulus responsive to receiving the one or more wireless commands.

* * * * *